July 5, 1960 E. B. PARKER Plant Pat. 1,957
CHRYSANTHEMUM PLANT
Filed Oct. 5, 1959
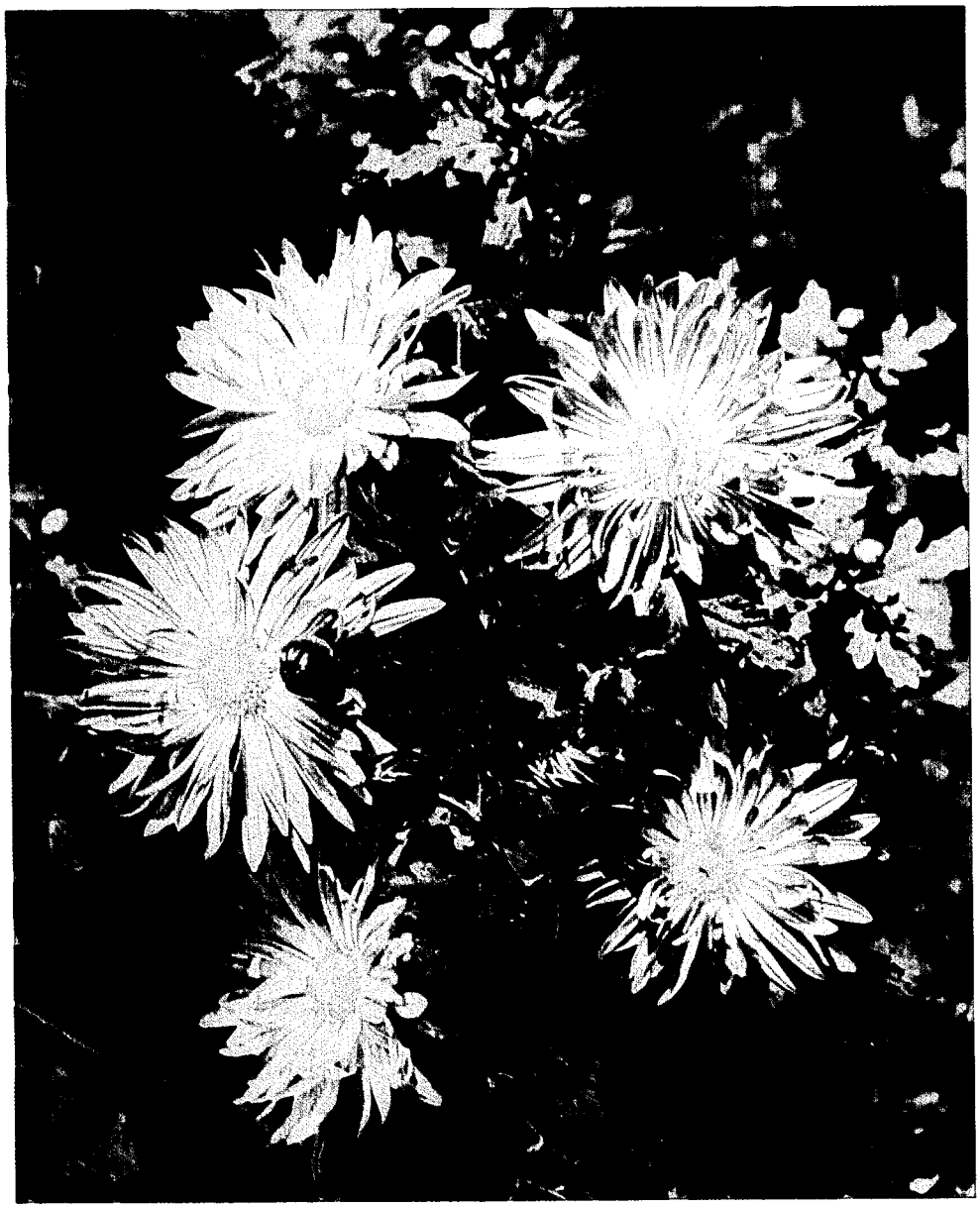
INVENTOR.
ELIZABETH B. PARKER
BY John Joseph Hall
ATTORNEY.

United States Patent Office

Plant Pat. 1,957
Patented July 5, 1960

1,957

CHRYSANTHEMUM PLANT

Elizabeth B. Parker, Los Angeles, Calif.

Filed Oct. 5, 1959, Ser. No. 844,601

1 Claim. (Cl. 47—60)

The present invention relates to a new and distinct variety of chrysanthemum plant obtained by first crossing the unpatented yellow spider chrysanthemum variety "Yellow Knight" with the unpatented chrysanthemum variety "Lilac Spoon" to produce an unnamed and unpatented orchid pink spoon chrysanthemum. This resulting orchid pink spoon chrysanthemum was then crossed with an unnamed and unpatented bronze daisy chrysanthemum which produced the present new and distinct variety of chrysanthemum plant.

The object of these crossings was to obtain a new and different chrysanthemum variety having a sweet fragrance which would last for the life of the flower and a variety having a new and unusual color. The resulting variety is an entirely new and distinct chrysanthemum plant which can be easily distinguished from its parents and from any other variety of chrysanthemum plant known to me by the following characteristics of my new variety.

This variety has a honey sweet fragrance which lasts for the life of the flower, approximately three to four weeks. This fragrance persists for the same length of time, three to four weeks, even after the flowers have been cut.

My new variety produces relatively large single flowers, 3 inches or more in diameter in the absence of any disbudding. Slight disbudding will produce flowers 3 to 5 inches in diameter. The flowers have a beautiful two tone coloration, which is one of the main characteristics of my new variety.

The center and inside of the petals of the mature flower have a color of Sulphur Yellow beginning at the proximal or central part of the petals which changes in shade to a Daphne Pink in the distal or outer portion of the inside of the petals. The Daphne Pink coloration of the petals comprises a portion of about ⅔ to ¾ of the entire inside of the petals with the remainder having the Sulphur Yellow coloration.

The outside of the petals has a color of Marguerite Yellow in the proximal or central portion which shades into a color of Tourmaline Pink as the distal or outer part of the petals is approached. The distal portion having the Tourmaline Pink coloration comprises about ¾ of the entire outside of the petals and the remaining ¼ of the petals has the Marguerite Yellow coloration.

At the budding stage of the present variety, the inside of the bud has an Indian Lake coloration and the outside of the bud has a Rosolane Purple coloration.

The height of the plant, 32 to 34 inches tall, is greater than either of its parents, and has a natural cascade. It can be supported to produce an upright. My new variety has a distinct cluster habit, with heavy flowering all along the stem and an unusually large number of buds, up to 30 and more.

The blooming period begins much earlier than that of the bronze daisy parent, beginning in the first week of October and ending in the latter part of November.

This new variety was cultivated in the frost free climate of Los Angeles, California. I have exposed my new variety to mildew and found it to be mildew-resistant.

I have performed asexual reproduction of my new variety of chyrsanthemum plant by cuttings through several succeeding generations at Los Angeles, California. All of the foregoing characteristics and distinguishing features of this new variety were transmitted true to form through each of the succeeding generations.

The accompanying color photograph shows typical specimens of the vegetation, flowers, and buds of my new variety.

A detailed description of my new variety follows, with all references to color being in accordance with Ridgway's Color Standards and Nomenclature.

Parentage: An unnamed and unpatented orchid pink spoon crossed with an unnamed and unpatented bronze daisy.

Classification: Single spoon.

Growth: A vigorous growing habit which cascades but can be supported to produce an upright growth and can be made bushy by pinching.

Cold resistance: Since the plant was cultivated in a frost free climate, no testing was made of cold resistance.

Mildew resistance: The plant is not sensitive to mildew.

Blooming period: From the first week in October until the latter part of November under the climatic conditions prevailing in Los Angeles, California.

*Flower*

Bud: The bud remains elongated and the center does not show until the petals begin to open. Color: inside of bud—Indian Lake, Plate 26; outside of bud—Rosolane Purple, Plate 10.

Bloom:

*Size.*—3 inches and more in diameter; slight disbudding produces blooms of 5 inches in diameter.

*Stem.*—Willowy and cascades readily.

*Form.*—Single spoon.

*Petalage.*—2 to 3 rows of long petals which are slightly rolled close to the proximal or central part of the flower.

*Fragrance.*—A honey sweet fragrance lasting for the life of the flower, 3 to 4 weeks, even when cut.

*Petals.*—Texture—smooth. Form—oval.

*Color.*—Center of flower—Sulphur Yellow, Plate 5. Inside of petals, proximal part—Sulphur Yellow, Plate 5. Inside of petals, distal part—Daphne Pink, Plate 38. Outside of petals, proximal part—Marguerite Yellow, Plate 30. Outside of petals, distal part — Tourmaline Pink, Plate 38.

*Plant*

Form: Medium height.

Growth: A vigorous cascade which can be made bushy by pinching or can be supported to be upright.

Foliage: Clean, mildew resistant, and lush with a sage-like aroma produced when the foliage is bruised.

*Size.*—3 to 5 inches leaf length.

*Quantity.*—Average.

*Texture.*—Medium grain.

*Color.*—Upper side — Elm Green, Plate 17. Reverse side—Light Elm Green, Plate 17.

I claim:

A new and distinct variety of chrysanthemum plant, substantially as shown and described herein, characterized particularly as to novelty by the honey sweet fragrance of its flowers, the long duration of the fragrance, the cluster habit and large number of blooms, the distinctive two-tone coloration of the petals of the open flower, having in the proximal portion of the inside of the petals a Sulphur Yellow color tonality shading to Daphne Pink as the distal portion of the inside of the petals is approached, and in the proximal portion of the outside of the petals a Marguerite Yellow color tonality shading to Tourmaline Pink as the distal portion of the outside of the petals is approached, and the resistance to mildew of the plant.

No references cited.